(12) United States Patent
Rosenfeld

(10) Patent No.: US 7,189,076 B1
(45) Date of Patent: Mar. 13, 2007

(54) DENTURE AND PROCESS FOR MANUFACTURING ARTIFICIAL TEETH FOR DENTURES

(76) Inventor: Mark D. Rosenfeld, 1112 Colorado Blvd., Los Angeles, CA (US) 90041

( * ) Notice: Subject to any disclaimer, the term of this patent is extended or adjusted under 35 U.S.C. 154(b) by 407 days.

(21) Appl. No.: 10/774,085

(22) Filed: Feb. 5, 2004

Related U.S. Application Data

(60) Provisional application No. 60/445,576, filed on Feb. 6, 2003.

(51) Int. Cl.
*A61C 13/08* (2006.01)
*A61C 8/00* (2006.01)

(52) U.S. Cl. .............. 433/202.1; 433/203.1; 433/201.1; 433/212.1

(58) Field of Classification Search .......... 433/202.1, 433/203.1, 212.1; 264/19, 20; 106/35
See application file for complete search history.

(56) References Cited

U.S. PATENT DOCUMENTS

| | | | |
|---|---|---|---|
| 3,975,203 A | 8/1976 | Dietz | |
| 4,131,597 A | 12/1978 | Bliiethgen et al. | |
| 5,346,397 A | 9/1994 | Braiman | |
| 5,447,967 A | 9/1995 | Tyszblat | |
| 5,621,035 A | 4/1997 | Lyles et al. | |
| 5,906,490 A * | 5/1999 | Kramer Primus et al. ............................................................ 433/203.1 |

* cited by examiner

Primary Examiner—Cris L. Rodriguez
Assistant Examiner—Candice C. Stokes
(74) Attorney, Agent, or Firm—Wagner Anderson & Brig; John E. Wagner

(57) ABSTRACT

A method of making an artificial tooth for a denture and the tooth so made, the method including making a form tooth of a plastic tooth or an existing denture tooth, using the form tooth to make a mold form, placing a thin layer (1 mm) of polycarbonate incisal material in the bottom of the mold form and conforming the material to the mold form, subjecting the layer of incisal and body material to a vacuum and then to a curing light in an oxygen-free atmosphere, adding additional layers of approximately 2 mm of the incisal and body material and exposing each layer to a vacuum and light curing step as described above until the mold form is full. The tooth is then removed from the mold form and again exposed to a vacuum and light curing step.

18 Claims, 2 Drawing Sheets

DENTURE AND PROCESS FOR MANUFACTURING ARTIFICIAL TEETH FOR DENTURES

REFERENCE TO RELATED APPLICATION

This Non-Provisional Patent Application claims benefit of U.S. Provisional Patent Application Ser. No. 60/445,576 filed Feb. 6, 2003, and hereby claims the benefit of the embodiments therein and of the filing date thereof.

BACKGROUND OF THE INVENTION

This invention relates to the manufacture of artificial teeth for installation in metal or plastic base installed in the wearer's mouth. The teeth and the base constitute a denture which may include any number of teeth up to and including the entire upper or lower dentures or plates.

Currently, such artificial teeth are usually formed of one of two materials. Either they are of porcelain, which has been recognized as being too hard, or they are of a plastic material, which is too soft. Porcelain teeth are typically formed of molded porcelain. Since porcelain is quite brittle, in addition to being very hard, porcelain teeth are subject to mechanical failure from cracks. The other principal disadvantage of porcelain teeth is that, because of their hardness, they tend to wear or damage opposing natural dentition.

Plastic teeth have been more popular than porcelain because of the above disadvantages. But since they are softer, they tend to wear away rapidly. As they become worn, they no longer exert the normal force on the opposing natural dentition, permitting the natural teeth to move, and throwing off the patient's bite and function. Many efforts have been made to produce plastic materials which are harder and less susceptible to wear but none are comparable to natural dentition.

In recognition of the above problems, many workers have sought to employ various polyceramic mixtures and similar materials in an effort to provide a suitable denture material, which has hardness closer to natural dentition.

Patents describing composition intended for use in dental applications include:

U.S. Pat. No. 3,975,203 to Dietz
U.S. Pat. No. 4,131,597 to Bluethgen
U.S. Pat. No. 5,346,397 to Braiman
U.S. Pat. No. 5,447,967 to Tyszblat
U.S. Pat. No. 5,621,035 to Lyles The above listed patents are merely exemplary of the many patents issued in this field.

SUMMARY OF THE INVENTION

Applicant has provided a method of making artificial teeth which are harder than plastic but not as hard as porcelain. Materials have become available described as polycarbonate dimethacrylate and marketed by Pentron Laboratories Technologies and sold under the names of Sculpture® and Sculpture® Plus which are designed to create metal-free, restorative dental composites.

It occurred to applicant that the Sculpture® material, which is useful for restorative dental composites, might also be used to produce entire new artificial teeth. Using the Sculpture® Plus material applicant made excellent artificial teeth by the following:

1) using as a mold an existing tooth or a molded plastic tooth, a mold form of impression material is produced;

2) a thin layer (1 mm) of Sculpture® Plus incisal material is placed in the bottom of the mold form;

3) this layer is cured by exposure first for five minutes to a vacuum in a nitrogen atmosphere and then for three more minutes to a curing lamp in a vacuum, also in a nitrogen atmosphere;

4) subsequent layers (approximately 2 mm) are built up in the mold form, exposed to the same curing process as above, until the mold form is full coloring each layer as desired;

5) removing the tooth from the mold form and subjecting the tooth to the same curing process as above;

6) inspecting the tooth for voids and filling any voids with incisal material and smooth or buff;

7) create retention holes in the bottom of the tooth;

8) lightly blast the tooth with white aluminum oxide and rinse or steam clean;

9) glaze, if desired, and cure the tooth in nitrogen atmosphere for nine minutes; and 10) cure the tooth in a heat-curing oven for approximately twenty minutes.

BRIEF DESCRIPTION OF THE DRAWINGS

This invention may be more clearly understood with the following detailed description and by reference to the drawings in which.

DETAILED DESCRIPTION OF THE PREFERRED EMBODIMENT

A survey of the materials available for forming teeth for dentures disclosed that most had significant disadvantages. A proprietary material of Pentron Laboratories Technologies, 53 North Plains Industrial Road, Wallingford, Conn. 06492, sold under the name "Sculpture®", was found to be the most satisfactory in that it is stain resistant, somewhat shock absorbing, and has wear characteristics similar to natural teeth. In working with this and other materials, the applicant developed artificial teeth and a process for making such teeth, which resulted in a greatly improved product, compared with those presently in use.

More recently, Pentron Laboratories Technologies has developed an improved dental composite now identified as Sculpture® Plus, which is believed to provide superior chip, stain and wear resistance. The use of this material results in a modification of the process described below. These modifications will be discussed in comparison with the process using the composition described as Sculpture®. Both materials use an indirect composite such as a polycarbonate dimethacrylate stated to be a proprietary material of Pentron Laboratories.

When a new denture is to be provided for a patient, the dentist designs the denture for the patient, choosing the shape and color of the denture teeth to be made. This specification is supplied to a dental laboratory that proceeds to manufacture the teeth according to the dentist's design. The process of creating new artificial teeth is essentially the same irrespective of which, or how many, teeth are to be made. Teeth from an existing denture can be used effectively as a die to form molds for the new teeth or, if such teeth are broken, excessively worn, or unavailable, new plastic teeth suitable as a die can be made by an existing well known process. Where possible or available, stone molds of the patient's original teeth can be used. This would make it possible to duplicate the shape of the patient's natural teeth.

Figure 1:
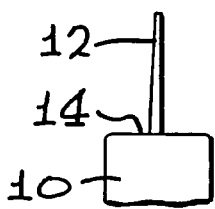
FIG. 1 is an enlarged perspective view of an original denture tooth or newly fabricated plastic tooth with a handle attached.

Initially, such an old denture tooth or plastic tooth used as a die has fastened to its bottom side a plastic stem or small handle by means of a suitable adhesive such as Zapit® from Dental Ventures of America (1-800-228-6696). This is shown in FIG. 1 wherein tooth 10 has affixed to itself a plastic handle 12 by means of a suitable adhesive 14. Zapit® has been found satisfactory since it sets up quickly and breaks off cleanly.

Figure 2:
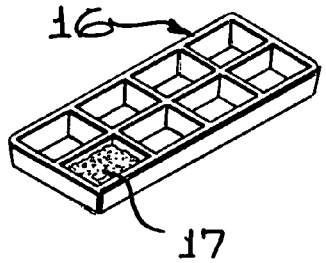
FIG. 2 is a perspective view of a tray for holding molds for teeth.

It has been found useful to create a multi-position mold form by cutting an ice cube tray in half horizontally to create a series of small mold forms of essentially identical depth. Other ways to create mold forms could be used. The mold, which may be formed in the aforementioned ice cube tray 16 or other mold form is then formed by squeezing into one of its divisions 17 enough impression material, such as "Panasil Contact Plus™" to fill the division to the desired depth. See FIG. 2.

Next, a small amount of the impression material is applied with a finger to the surface of the form tooth. Holding the plastic handle, the form tooth is then pushed into the impression material up to the base, leaving the bottom and the adhesive area exposed. It has been found that the small finger applied layer of impression material tends to prevent bubbles from occurring in the molds. The die or form tooth is left in the mold for at least ten minutes and then removed. The mold or set impression 18 is then removed from the tray 16.

Figure 3:
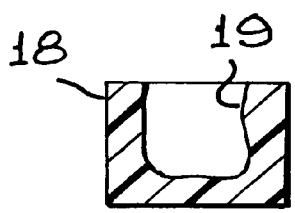
FIG. 3 is a sectional view of a mold after the original tooth has been removed.

FIG. 3 is a sectional view of the set impression after removal of the tooth from the mold 18 leaving an impression 19. The above process is repeated for each tooth required for the desired denture. The mold 18 is for a specific tooth only and is numbered and labeled for identification.

Figure 4:
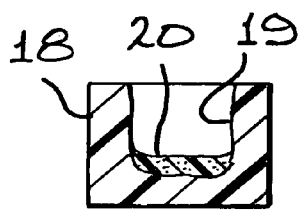
FIG. 4 is a sectional view of the mold of FIG. 3 as incisal material is added.
Figure 5:
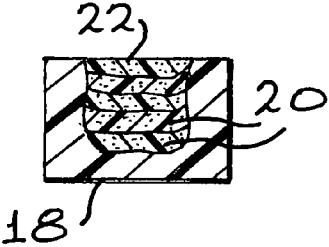
FIG. 5 is a sectional view of the mold of FIG. 4 after additional layers of incisal material have been added.

FIG. 4 is a side elevational view, partly in section, showing the mold 18 with a small amount of the clear incisal 20 (indirect composite material) placed in impression 19, such as the Sculpture® or Sculpture® Plus material referred to above, which is smashed or forced in and adapted in small amounts to the contour of the mold 18 by means of a small instrument which serves as a pestle, while the mold serves as a mortar to conform the clear incisal to the impression 19. This layer of sculpture material is then cured for ten seconds under a curing light. Other layers 22 of clear incisal sculpture material (about 1 mm at a time) are added until the mold is filled and each layer is cured for ten seconds under a curing light. See FIG. 5. Color material is added as required for each increment. Normally, darker color is added for about the lower one-half of the height of the tooth and lighter color for the upper one half to match the pattern of natural teeth. A very small amount of thinning liquid, such as Sculpture® Plus Thinning Liquid, may be used to prevent the incisal material from sticking to the instrument used for adaptation. After the incisal color is in the mold (with the body and sides ⅓ of the way down and tapped very thin), body color is added and cured in the mold until the mold is full.

The tooth is then carefully removed from its mold 18 while under light cure and placed in a separate light curing oven for nine minutes. Following this curing step, the tooth is allowed to cool and inspected for any voids or other imperfections, and any such voids that are found are filled. The tooth is then lightly smoothed with a white rubber wheel.

When Sculpture® Plus material is used, it has been found useful to subject an initial 1 mm layer to a five minute vacuum cycle (approximately 29 in. Hg) in a nitrogen (oxygen-free) atmosphere followed by a three minute vacuum (approximately 29 in. Hg) segment with exposure to curing light. Subsequent layers may be approximately 2 mm or somewhat thicker until the mold is filled. All the foregoing described steps are preferably performed in a Sculpture® curing light which is a proprietary product of Pentron Laboratories Technologies and which automatically provides the described vacuum, light (and heat) curing cycles in a nitrogen atmosphere.

The vacuum applied in a nitrogen atmosphere during both the initial stage and the light-cure stage (which includes significant heat from the lamps) provides enhanced bonding between layers and removes flaws or voids.

In a final cure cycle, after the tooth is removed from the mold, the above process is followed with the cure chamber purged of oxygen using nitrogen. This produces a hard outer surface receptive to polishing.

Figure 6:
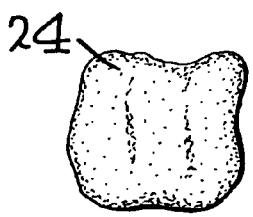
FIG. 6 is a side elevational view of a tooth after being removed from the mold and ready for inspection.

FIG. 6 is a side elevational view of a tooth 24 following filling any voids and buffing with the rubber wheel and ready for inspection.

A further step is to create one of more retention holes in the bottom of the tooth, undercutting them as shown in FIGS. 7, 8, 9, or 10. This process has been named "MECHANICAL ORB RETENTION (M.O.R.)".

Figure 7:
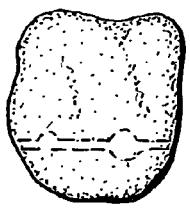
FIG. 7 is a side elevational view showing a posterior tooth following the curing step with a transverse retention hole created across the bottom base.

FIG. 7 is a side elevational view of a posterior tooth following inspection and with a retention hole created on its base. The holes are on the proximal sides of the base to create a tunnel effect. A half round #1 or #2 round burr may be used on the sides.

Figure 8:
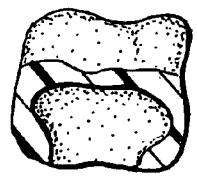
FIG. 8 is a side elevational view of a posterior tooth, partly in section, with the base undercut to provide a retention cavity.

FIG. 8 shows a tooth similar to that of FIG. 7 but is partly in section showing an undercut retention hole.

Figure 9:
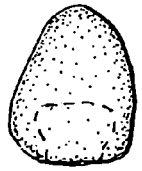
FIG. 9 is a side elevational view of an anterior tooth with its base undercut.

FIG. 9 is a side elevational view of an anterior tooth made according to the above-described process and having a retention hole on the bottom base shown in dashed outline. The anterior teeth do not have the holes in the sides, but the bottom retention hole includes an internal undercut. These internal holes should not be visible from the front of the tooth when held up to light because the pink acrylic substrate may show when the denture is completed.

Next, the tooth is lightly sand blasted with an abrasive such as white 50 micron aluminum oxide followed with a thorough rinse in distilled water in an ultrasonic cleaner for about two minutes or steam cleaned. The tooth is then dried.

After the cleaning step, the tooth is stained, if needed or desired, and a small amount of glaze, such as Sculpture® Plus LD Glaze, is applied with a brush or hand polish with Sculpture®Glo.

Figure 10:
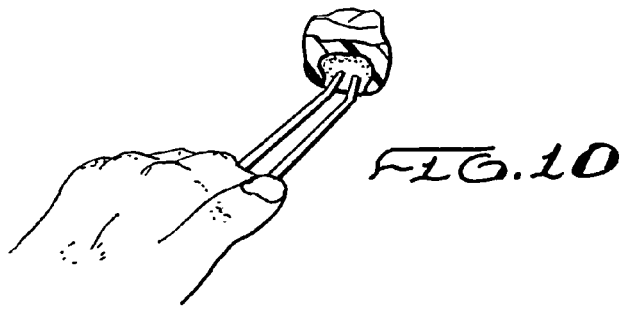
FIG. 10 is a perspective drawing of a tooth supported by tweezers in the hand of an individual.

Following the application of the glaze material, the tooth is held by a suitable holder such as tweezers in the retention hole, as shown in FIG. 10, and is seated on a glazing dome (which may be the Sculpture® curing light described above), base side down. Nitrogen gas is introduced into the dome and the tooth and dome are exposed to a light curing oven under vacuum for another nine minutes, following which they are exposed to a heat-curing oven for twenty minutes. The teeth are then removed from the curing oven and allowed to cool.

The tooth is now inspected and if at all tacky, buffed lightly with a chamois wheel.

The tooth is then completed and is ready to be installed in a substrate, which will vary depending upon the location, number of teeth, etc. These factors also influence whether the substrate is partly of metal. In any event, the tooth will normally be molded into a substrate consisting of pink acrylic, which flows into the retention hole or holes formed as described, holding the tooth or teeth very securely.

Figures 11, 11A:
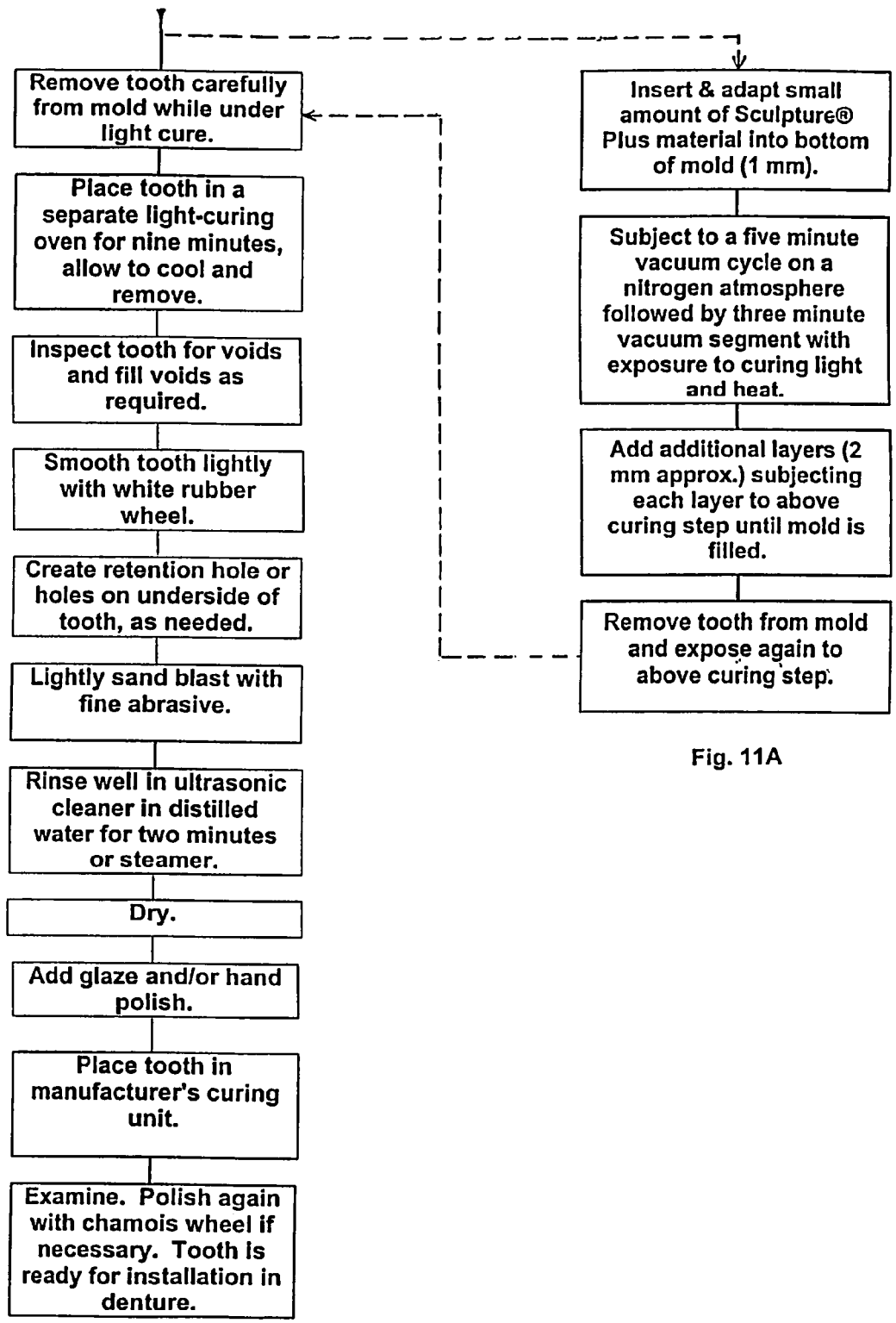
FIG. 11 is a flow diagram showing the steps of manufacturing a tooth according to the invention.
FIG. 11A is a flow diagram indicating a modification of the steps of FIG. 11.

FIG. 11 is a flow diagram showing in detail the process described above using Sculpture® incisal material.

FIG. 11A is a flow diagram showing a modification of the process of FIG. 11 when using Sculpture® Plus incisal material.

The above-described embodiments of the present invention are merely descriptive of its principles and are not to be considered limiting. The scope of the present invention instead shall be determined from the scope of the following claims including their equivalents.

I claim:

1. A method of making an artificial tooth for placement in a denture comprising the steps of:
   a) making a mold form of the desired tooth;
   b) inserting in the mold form a thin layer polycarbonate dimethacrylate incisal material and forcing said material into the contour of the mold;
   c) subjecting said thin layer to a curing step including a first time segment of vacuum followed by a second time segment of vacuum and light curing including heat;
   d) adding additional thin layers of incisal material and subjecting each layer to the curing process of step c) until the mold is full;
   e) removing the tooth from the mold form and subjecting the tooth to the curing step described in step c) to complete the tooth.

2. A method as claimed in claim 1 wherein following step e) retention holes are formed in the lower part of said tooth.

3. A method as claimed in claim 1 wherein following step e) said tooth is inspected for voids and any such voids are filled with polycarbonate dimethacrylate material.

4. A method as claimed in claim 3 wherein following filling any voids in said tooth, said tooth is lightly blasted with abrasive and rinsed in distilled water in ultrasonic cleaner.

5. A method as claimed in claim 4 wherein following said rinsing step said tooth is glazed and further cured in a substantially oxygen-free atmosphere and light for approximately nine minutes.

6. A method of manufacturing an artificial tooth for placement in a denture comprising the steps of:
   a) making a form tooth;
   b) placing the form tooth in a mold form of impression material;
   c) removing the form tooth from the mold form after the form tooth has been in the mold form for at leastf substantially ten minutes;
   d) inserting in the mold form a thin layer of polycarbonate dimethacrylate incisal material and forming said material into the contour of the mold;
   e) subject said thin layer to a five minute vacuum of approximately 27 in. of Hg followed by a three-minute segment of approximately 29 in. of Hg vacuum and light curing including heat;
   f) add additional layers of 2 mm or more thickness and subject each layer to the curing process of step 5) until the mold is full; and
   g) removing the tooth from the mold form and subjecting the tooth to the curing step described in step e.

7. A method as claimed in claim 6 wherein following step g) said tooth is inspected for voids and any such voids are filled with polycarbonate dimethacrylate material.

8. A method as claimed in claim 6 wherein following step g said tooth is inspected for voids and any such voids are filled with polycarbonate dimethacrylate material.

9. A method as claimed in claim 6 wherein following step g) retention holes are formed in the lower part of said tooth.

10. A method of manufacturing an artificial tooth for placement in a denture comprising the steps of:
    a) making a mold of the desired tooth;
    b) making a mold form of impression material;
    c) placing a small layer of impression material on the surface of the tooth mold;
    d) pushing the mold into the mold form up to the base and leaving the bottom and glue area exposed;
    e) removing the tooth mold from the mold form after the tooth mold has been in the mold form for at least substantially ten minutes;
    f) inserting in the mold form a thin layer of indirect composite incisal material and forcing said material into the contour of the mold;
    g) subjecting said thin layer to a five minute vacuum of approximately 27 in. of Hg followed by a three-minute segment of approximately 29 in. of Hg vacuum and light cure;
    h) adding additional layers of indirect incisal composite material and subjecting each layer to the curing process of step g until the mold is full;
    i) removing the tooth from the mold form and subjecting the tooth to the curing step described in step g.

11. A method as claimed in claim 10 wherein following step i) retention holes are formed in the lower part of said tooth.

12. A method as claimed in claim 10 wherein following step i) said tooth is inspected for voids and any such voids are filled with indirect composite material.

13. A method as claimed in claim 12 wherein retention holes are formed in the lower part of said tooth.

14. A method as claimed in claim 13 wherein said tooth is blasted with a fine abrasive and rinsed.

15. A method for manufacturing an artificial tooth for placement in a denture comprising the steps of:
    a) making a mold of the desired tooth;
    b) making a mold form of impression material,
    c) gluing a handle to the mold;
    d) placing a small layer of impression material on the surface of the tooth mold;

e) holding the handle, pushing the mold into the mold form up to the base and leaving the bottom and glue area exposed;
f) removing the tooth mold from the mold form after the tooth mold has been in the mold form for at least substantially ten minutes;
g) inserting in the mold form a thin layer of an indirect composite incisal material and forcing said material into the contour of the mold;
h) curing said thin layer under light;
i) repeating steps g and h as required until the mold form is filled, adding color as required to each layer to complete the tooth;
j) removing the tooth from the tooth mold and placing the tooth in a light-curing oven for nine minutes;
k) inspecting the tooth for voids or other imperfections and fill any voids with incisal material;
l) lightly smooth or buff tooth;
m) creating retention holes in bottom of tooth;
n) lightly blast tooth with white aluminum oxide and rinse in distilled water in ultrasonic cleaner approximately two minutes or steam clean;
o) dry tooth and stain if needed;
p) seating tooth in curing unit, base side down, and glaze;
q) cure in nitrogen atmosphere and light for nine minutes;
r) cure in heat-curing oven twenty minutes;
s) remove from oven and allow to cool; and
t) inspect and buff with chamois wheel, if needed.

16. An artificial tooth for placement in a denture and formed in a mold comprising:
   a plurality of layers of indirect composite incisal material, each layer of which is subjected in said mold to a curing process including exposure to vacuum and light-curing steps in an oxygen-free atmosphere;
   a further curing step after removal of the tooth from the mold including exposure to a vacuum and light-curing step in an oxygen-free atmosphere; and
   forming retention holes for anchoring said tooth to a denture.

17. An artificial tooth as claimed in claim 16 wherein following said vacuum and light-curing step said tooth is blasted with a fine abrasive and rinsed.

18. An artificial tooth as claimed in claim 16 wherein said tooth has a glazed and/or polished surface.

* * * * *